(12) United States Patent
Gamboa

(10) Patent No.: US 7,559,948 B2
(45) Date of Patent: Jul. 14, 2009

(54) FENESTRATED ASYMMETRIC INTRACARDIAC DEVICE FOR THE COMPLETION OF TOTAL CAVOPULMONARY ANASTOMOSIS THROUGH CARDIAC CATHETERIZATION

(76) Inventor: Ricardo Gamboa, Calle 8 No823 Entre 523 Bis Y 524, Tolosa, Buenos Aires (AR) 1900

( * ) Notice: Subject to any disclaimer, the term of this patent is extended or adjusted under 35 U.S.C. 154(b) by 421 days.

(21) Appl. No.: 10/663,777

(22) Filed: Sep. 17, 2003

(65) Prior Publication Data

US 2005/0060026 A1 Mar. 17, 2005

(51) Int. Cl.
*A61F 2/06* (2006.01)
(52) U.S. Cl. .................... 623/1.35; 623/1.3
(58) Field of Classification Search ............. 623/1.1, 623/1.13, 1.3, 1.31, 1.35, 1.46, 1.16
See application file for complete search history.

(56) References Cited

U.S. PATENT DOCUMENTS 7,131,991 B2 11/2006 Zarins .................... 623/13
2003/0204242 A1* 10/2003 Zarins et al. ............ 623/1.16

* cited by examiner

*Primary Examiner*—Paul B. Prebilic
*Assistant Examiner*—Joshua Levine
(74) *Attorney, Agent, or Firm*—Andrew Wilford

(57) ABSTRACT

An intracardiac stent for total cavopulmonary anastomosis has a large-diameter plastic-coated mesh conduit with circular-section lower portion and a progressively flattened upper portion of the same cross-sectional area as the lower portion. Both portions extend along a curved axis. The upper end is bifurcated into two smaller-diameter branches, one of which is also of circular section and extends in an arc along the axis. The other branch is flattened and extends obliquely to the side so as to give the stent the shape of a lopsided Y. In use the upper and lower portions are lodged in the heart with a lower end of the lower portion fitted to the lower vena cava and hepatic vena, the one branch tightly fitted to the left pulmonary artery and blocking the main pulmonary artery, and the other branch fitted to the base of the right pulmonary artery.

7 Claims, 6 Drawing Sheets

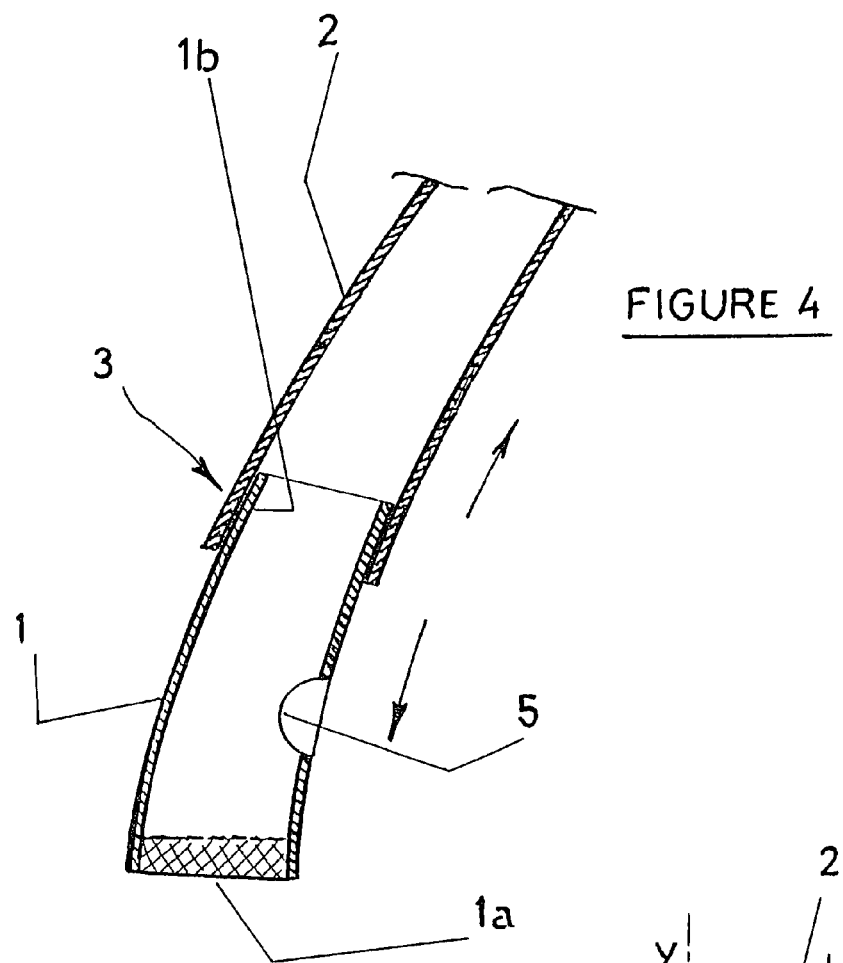
FIGURE 4
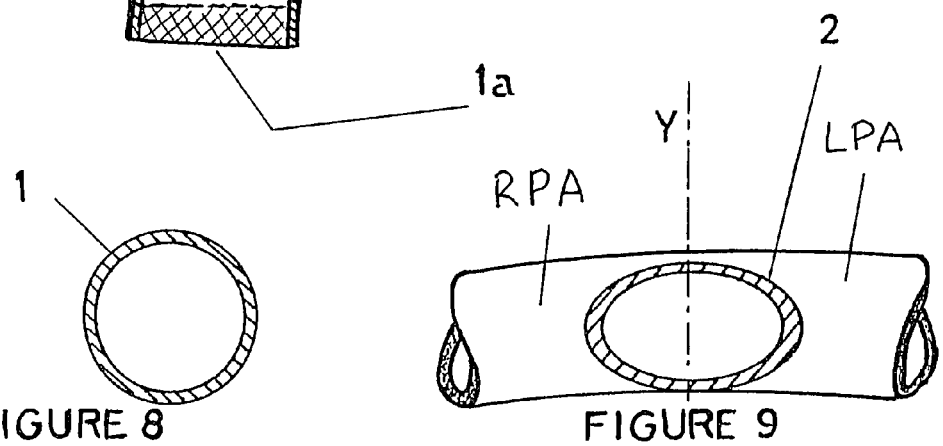
FIGURE 8
FIGURE 9

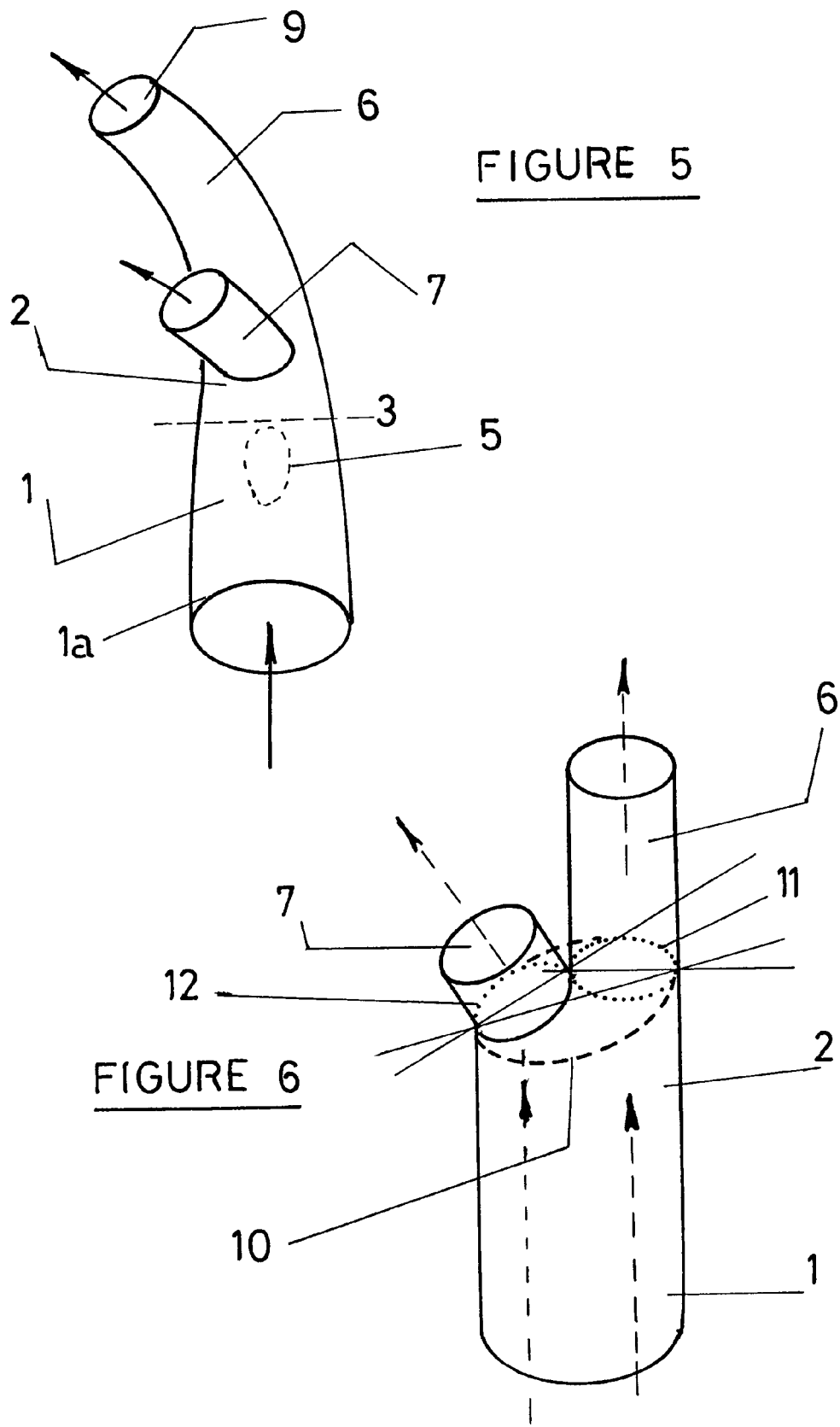

FENESTRATED ASYMMETRIC INTRACARDIAC DEVICE FOR THE COMPLETION OF TOTAL CAVOPULMONARY ANASTOMOSIS THROUGH CARDIAC CATHETERIZATION

FIELD OF THE INVENTION

The present invention relates to an intracardiac device for treatment of the following congenital heart diseases (C.D.) with univentricular physiology:

Single ventricle,
Tricuspid atresia,
Hypoplastic left heart syndrome (HLHS),
Pulmonary atresia with intact septum and hypoplasic right ventricle,
Transposition of the great vessels, with noncommitted ventricular septal defect and small right ventricle,
Double outlet right ventricle and poor anatomy,
Criss-cross heart,
Congenital right ventricular hypoplasia, and
Ebstein's malformation.

BACKGROUND OF THE INVENTION

Most of these CHDs need a multistep treatment strategy. Some of them (such as hypoplastic left heart syndrome) require a special therapy.

When the patient is born with single ventricle (classic C.D. of this pathology) and stenosis or pulmonary atresia that hinder pulmonary flow, in order to maintain a proper oxygenation, a prompt modified Blalock-Taussig anastomosis should be performed with a prosthesis tube of 4 mm between the subclavian artery and the homolateral pulmonary branch, usually on the left side.

If there is no pulmonary stenosis, a banding of the pulmonary artery to narrow the lumen, to limit the flow and the pressure transmitted to the pulmonary circuit, should be performed. This prevents the development of pulmonary hypertension that would prevent the patient from being well enough to undergo further surgical treatment.

A fenestrated asymmetric intracardiac device serves to do a total cavopulmonary anastomosis through cardiac catheterization. More particularly such an intracardiac device is used in pediatric cardiologic operations, more specifically to correct specific congenital heart disease in hemodynamic operations.

There are different congenital heart diseases (C.D.) with only one working ventricle available, so this disability necessitates a therapeutic strategy which allows the development of a special hemodynamic model. These cases are present in newborns with this cardiac malformation and it is absolutely necessary to correct it by means of surgery.

During the last decades different techniques have been introduced for the multistep preparation of the circulatory system, with the final aim of connecting the venous blood that comes from the heart through the superior and inferior vena cava with the pulmonary circuit, allowing oxygenation of blood. This involves performing a bypass to the right ventricle, because the non-existence or rudimentary structure of this C.D. does not allow one to perform its pump function of pulmonary circulation.

The goal is to maintain blood flow through a minor circuit with the pumping function of the only active ventricle. This circuit should have low resistance to flow, without obstruction sites, so that blood can flow properly, even if it is pumped with unnatural right heart venous pathways.

Under any of the two conditions described above, at the age of 6 or 8 months, patients should be subjected to a Bidirectional Glenn procedure. This procedure consists of the separation of the superior vena cava (SVC) from the right atrium (RA) and its connection with the right pulmonary branch (RPB). This way all the venous flow of the superior half of the body will flow directly to the pulmonary artery (PA) to become oxygenated without passing through the heart. This procedure is performed at this age because the head and the superior half of the body represent the 55% of the venous return. This is an open-heart procedure with cardiopulmonary bypass (CB).

The last step is to complete the total cavopulmonary connection (TCPC) at the age of 3 or 4 years old, by connecting the inferior vena cava to the pulmonary artery, also under cardiopulmonary bypass (CB). The surgical techniques have been substantially modified in the last decades, specially in this phase. Since the early Fontan-Kreutzer procedure, which consisted of joining the right atrium to the right pulmonary branch (atriopulmonary anastomosis) up to the current anastomosis with extracardiac tube between SVC and PA, several techniques have been tried.

This last-mentioned technique consists of the anastomosis of the inferior vena cava (IVC) to the right pulmonary branch (RPB) with the interposition of a Gore-Tex™ extracardiac prosthesis tube with a fenestration or hole in the RA as "discharge" in order to secure the postoperative cardiac output.

At this phase, the so-called "total cavopulmonary connection" (TCPC) is finished. Of late, some attempts have been made using a covered stent with a surgical catheterization to finish this last phase, and so avoid a new surgery, simplify the technique, minimize the risks as well as side effects.

These stents have an expandable tubular mesh made of different materials, such as a platinum-iridium, nickel-titanium, stainless-steel mesh and covered with an impermeable polymer, like expanded polytetrafluorothyelene (PTFE). With these devices, after performing the Bidirectional Glenn procedure, IVC is connected to SVC. The TCPC procedure with extracardiac tube as well as the procedure with the current stents have the inconvenience of supplying an unbalanced flow to the pulmonary circulation. Current stents have one or several fenestrations which allow discharge of blood from the circuit, if the hemodynamic condition is not ideal, allowing a right to left shunt at atrial level, so as to maintain the postoperative cardiac output. These openings or holes need to be closed or sealed when the patient's hemodynamic condition allows one to do so.

To show a better reference frame of the former state of the art, before this invention, FIG. 1 shows schematically a heart which suffers from these CHDs, before the Glenn procedure, and in FIG. 2 this same heart after the Glenn procedure.

The following acronyms are used in both figures:
RPA Right pulmonary artery
LPA Left pulmonary artery
SVC Superior vena cava
IVC Inferior vena cava
SHV Hepatic vein
Ra Right appendage
RA Right atrium
TV Tricuspid valve The following are bibliographical references of these known more recent techniques:

"Surgical Preconditioning and Completion of Total Cavopulmonary Connection by Interventional Cardiac Catheterization: A New Concept," (Heart 1996; 75: 403-409).

Through this technique the field to complete by catheterization the total cavopulmonary connection of high risk patients is carried out during the Glenn procedure.

A left banding is done between RA and SVC, setting a Gore-Tex™ tube with 3 to 7 perforations (multifenestrated) inside RA. During the next intervention, the banding is dilated with or without a Palmaz stent between SVC-AD, and the fenestrations are closed with Rashkind devices of 17 mm, used for the closure of the patent ductus arteriosus. If it is not possible to perform this technique, a covered stent inside a Gore-Tex™ tube is installed.

"A Novel Technique for Establishing Total Cavopulmonary Connection: From Surgical Preconditioning to Intervention Completion," (J. Thorc Cardiovasc Surg. 2000; 120; 1007-9).

This technique contemplates the experimental use of a cavo-caval anastomosis with a covered stent through cardiac catheterization. Previously, a side-to-end anastomosis between SVC and distal RPB with PTFE should be performed. SVC is left banded in its joint with RA. The next procedure is to introduce endovascularly a stent graft from the right internal jugular vein, fitting it through the SVC banding, between SVC-RPA joint and IVC over the hepatic vena end. Then the pulmonary cava-cava artery anastomosis is completed.

"Effect of Baffle Fenestration on outcome of the Modified Fontan Operation," (Circulation 1992; 86:1762-1769).

This technique shows the benefits of fenestration in the Fontan procedure in patients at high risk. This study compares a group of 91 patients in which a fenestration of 4 mm has been left in the intracardiac tube with 56 patients without fenestration. It was concluded that the fenestrated tube is associated with low mortality, less incidence of pleural effusion and less days in hospital.

Up to today none of these operation has shown optimal outcomes because in the long term a number of patients need different operations.

From the age of 6 approximately, the percentage of systemic venous return, which is kept up to the adult age, is reached. The 35% of the pulmonary flow of a healthy adult without C.D. is supplied by SVC and the 65% by IVC. The right lung, anatomically bigger, should receive approximately 55% of blood and the left lung, smaller, 45%. This implies a flow division from the IVC in 20% of the total (30.7% flow from IVC) that should run to the RPA, while the 45% left runs to the LPA.

With the C.D. corrective techniques currently known, it is not always feasible to guarantee a proper division of the pulmonary blood flow, resulting in a deficient supply according to the technique used in one or the other lung, usually the left one.

Another problem of the known corrective techniques with the devices mentioned above and which can result in serious inconveniences is the IVC transverse section in the grown up children which has an average of 18-20 mm, while the PA has an average diameter of 10-13 mm approximately. The known techniques and devices resolve this problem by connecting with a suture the upper end of the extracardiac conduit to the PA, and flattening it, which transforms a theoretically round section into a theoretically elliptical transverse section, resulting in an area decrease, and so increasing the flow resistance, if the speed of blood flow is reasonably constant.

The last problem is the longitudinal dimensions in case the device is intracardiac, because not all the patient's anatomies have the same dimensions and so the device should be adapted to the somatic growth.

OBJECT OF THIS INVENTION

The main target of this invention is to provided a covered stent or endoprostheses device to complete the total cavopulmonar connection or anastomosis through a cardiac catheterization procedure.

This device should be implanted in procedures performed in those CHDS which need univentricular correction. Previously, an anatomical preparation during the Bidirectional Glenn procedure should be done.

An intracardiac device is another object of this invention, which allows a best distribution of the blood flow dynamics, being able to feed between 30 to 35% of the blood flow from the IVC to the RPA and between 65 to 70% of the blood flow to the LPA, establishing a physiological distribution of the blood flow in both lungs, which the previous Bidirectional Glenn procedure brings to the right lung.

Yet another object of this invention is a covered stent or endoprostheses which allows one to stop the blood flow from the pulmonary artery trunk (in the case of banding of it) or to close the Blalock-Taussig anastomosis (in stenosis or pulmonary atresia cases).

Another object of this invention is an intracardiac device whose transverse sections allow to compensate the shape change (flattening of the transverse section) and to obtain a reasonable constant transverse section.

Yet another object is an intracardiac device invention which allows adaptation and compensation of the existing dimensional differences in the RA in different patients.

Yet another object is a device which allows blood to be fed from the IVC to the pulmonary artery where it joins with the trunk and the pulmonary right branch.

Yet another object is a device which allows to discharge the blood from the fenestration towards the RA in non ideal cases ("high risk patients").

Yet another object is a device which allows the physiological distribution of the pulmonary flow matched with the Bidirectional Glenn procedure, improving the existing models.

Yet another object is a device which allows the treatment of the pulmonary tree distortion, decreasing the total resistance.

Yet another object is a device is to set a blood flow with the smallest power losses with regards to the existing one.

Yet another object is a device is to contemplate the heart somatic growth by its left convexity curvature and the re-expansion of its diameters.

And, the final object is a device to draw the blood from the liver (IVC) towards both lungs, which is a physiological important circumstance which avoids the development of pulmonary arteriovenous fistulas.

SUMMARY OF THE INVENTION

The fenestrated asymmetric intracardiac device for the completion of total cavopulmonary connection through cardiac catheterization is characterized in that it has a bifurcated tubular conduit, whose parts are: a first lower portion and a second upper portion both centered on a curved or warped line or axis.

The first portion is a tubular mesh covered with an impermeable polymer with a curvature of between 35° and 45°, this first portion having in its lower end a substantially circular cross-sectional shape with a diameter between 16-20 mm, while in its upper end the first portion has a cross-sectional shape that is progressively flattened going upward so as to be substantially oval while being of uniform cross-sectional size or flow cross section along its length.

The side of this first portion is formed with a hole or fenestration that can be closed and that connects the interior of this conduit with the exterior. The lower end of this first portion can be formed by a mesh structure without polymeric cover, defining a permeable conduit end. This first lower portion is followed by the second upper portion which has a tubular mesh covered, at least in some parts, by an impermeable polymeric material and with a cross-sectional shape that is ever more oval going upward to end with an elliptical shape having a minor diameter between 10-13 mm.

Both transverse sections are substantially of the same area. After the second portion reaches a diameter smaller than 10-13 mm, it bifurcates into two branches, one of the branches being longer and of circular cross-sectional shape with a diameter between 10-13 mm and prolonging the warped axis with a posterior inclination, while the other branch is formed as a short obliquely backwardly diverging extension of substantially circular section with a diameter of 10-13 mm and forming with the long branch a deformed. "Y". The conduit having an overall length of between 60-75 mm, with the longer branch being between 18-25 mm long, and the short branch being between 4-8 mm long and having a wall portion that intercepts between 50%-70% of blood flowing up through the main tubular conduit from its lower end. The lower end of the first section defines a connection between the lower vena cava and the hepatic venous, with this tubular conduit lodged inside the right atrium and anchored in the joint of this structure and the IVC, while the long branch is lodged inside the left pulmonary artery in close contact with the internal walls thereof and forming an obstruction of the pulmonary artery trunk, while the short branch is lodged inside the source of the right pulmonary artery.

BRIEF DESCRIPTION OF THE DRAWING

The following drawing figures together with their description will illustrate this invention. This illustrated embodiment should be understood as one of the many possible constructions of the invention, not limiting its use, including possible equivalent means described, the scope of this invention being determined by the claims. Likewise, in this figures, the same references identify the same or equivalent means.

FIG. 4 shows a detail of the device in section.

FIG. 5 shows the same device turned 90% around its axis.

FIG. 6 shows schematically the cross-sectional areas, illustrating the concept of the division of the blood flow which runs up in IVC in the device.

FIG. 8, shows the section taken along line AA of FIG. 3, and

FIG. 9 shows the section taken along line BB of FIG. 3.

SPECIFIC DESCRIPTION

Figure 1:
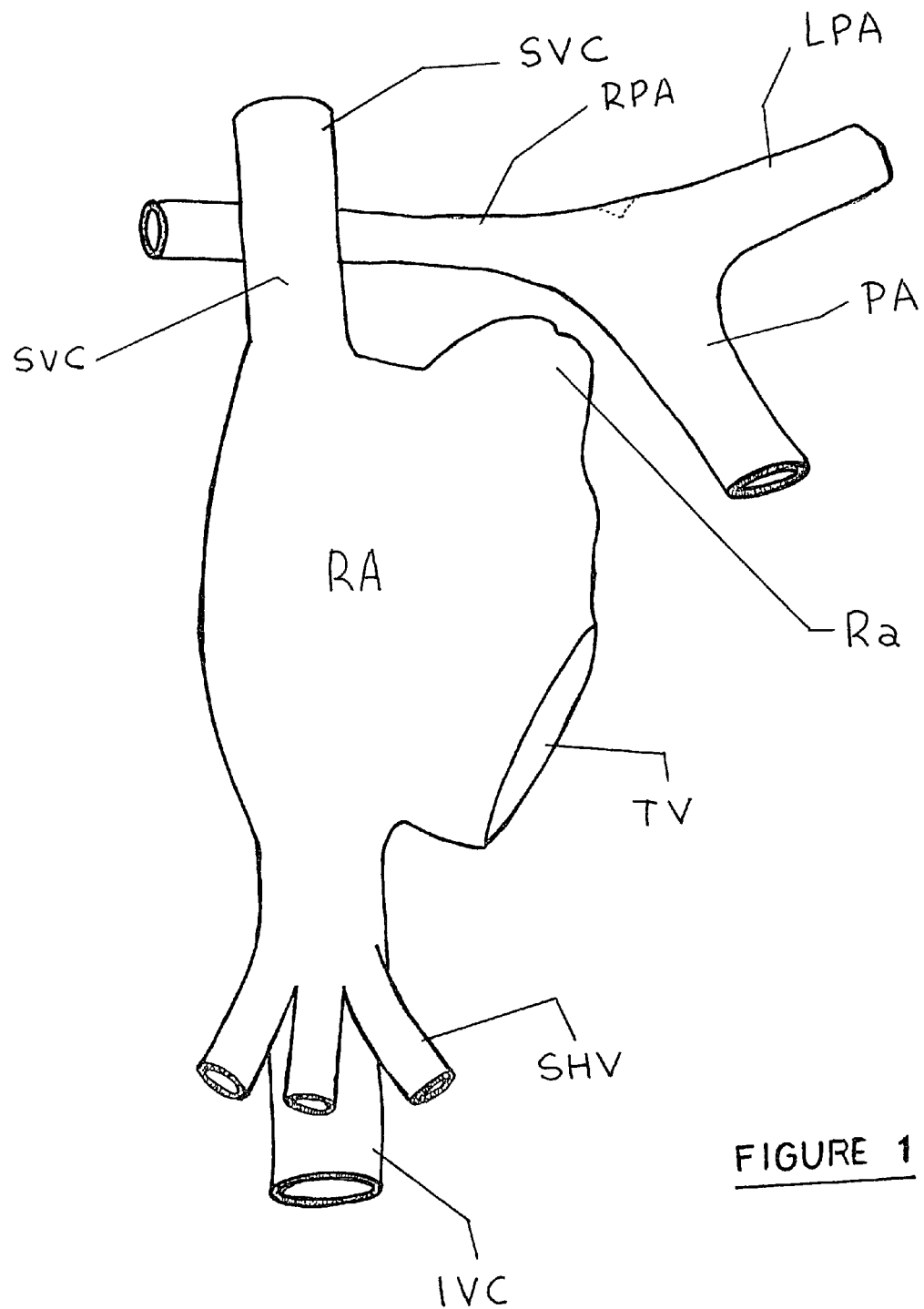
FIG. 1 shows schematically a heart with congenital C.D. as described above and showing only the area related to RA.

FIG. 1 shows schematically a RA of a heart with a characteristic congenital heart disease in its condition before a Glenn procedure.

Figure 2:
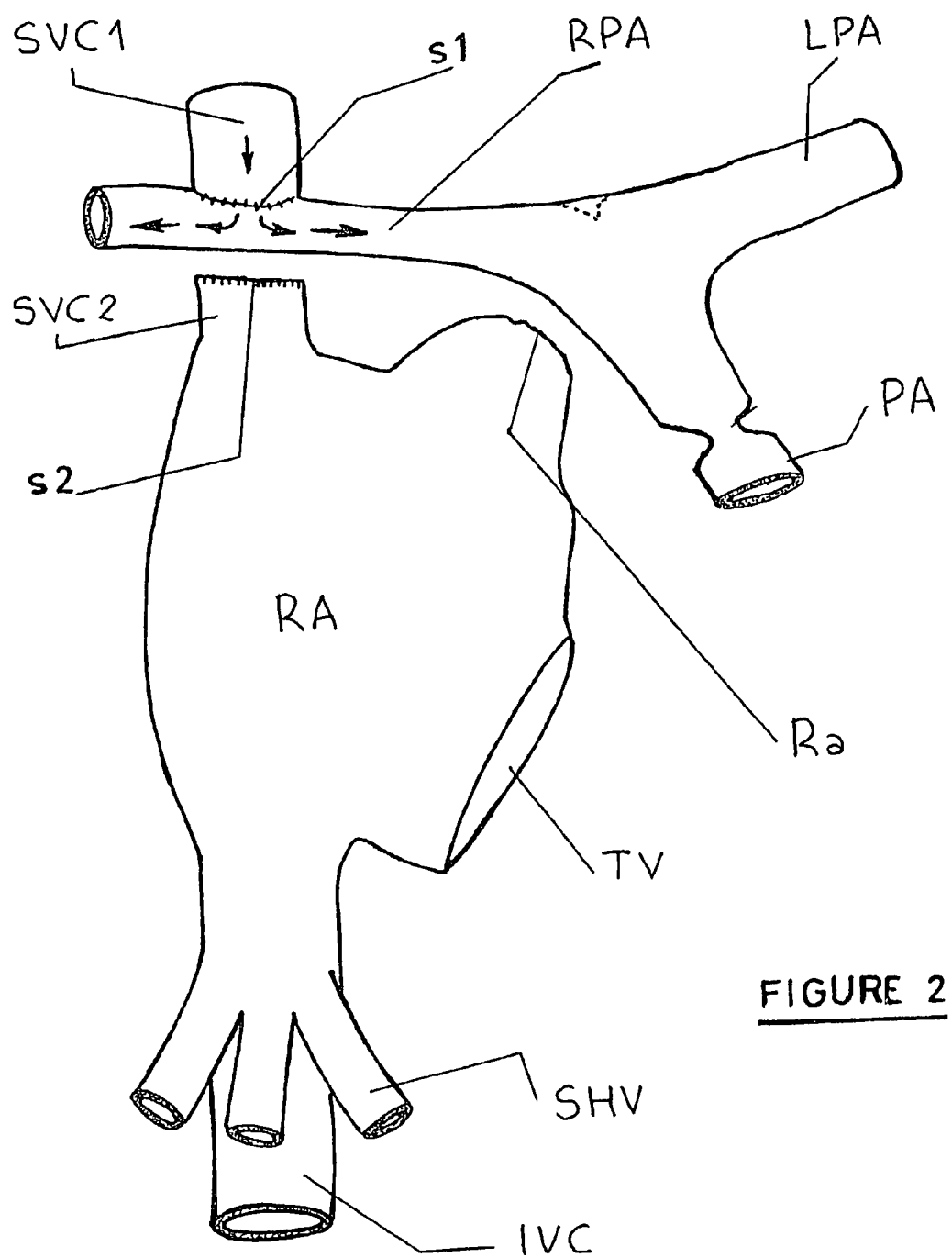
FIG. 2 shows the same heart portion as FIG. 1 which has undergone the Glenn procedure and banding in the pulmonary artery.

FIG. 2 shows the same RA after the Glenn procedure, which consists of the sectioning of SVC, suturing the upper section SVC1 to the RPA branch to join them at s1, while SVC2 is connected to RPA is closed at s2 with sutures. Previously the pulmonary artery has been banded at b.

With this operation the heart is ready for the next operations described above. The invention contemplates an asymmetric intracardiac device which is a covered stent or endoprostheses having a first lower section (1) and a second upper section (2). Both sections (1,2) are aligned on a common warped axis X-X and form a single tubular conduit.

The first lower section (1) is a mesh, like a stent mesh, that is to say a mesh made of metallic threads joined or welded and covered with an impermeable polymeric material, such as polytetrafluorothyelene (PTFE). The lower end or section (1a) of the lower portion (1) is preferably not covered and is inserted inside the IVC, allowing the mesh portion without cover to collect blood which comes from the SHV.

There can be two different parts that form these two sections (1,2). In one embodiment the lower section (1) is axially inserted inside the second section (2), the joining area is shown in reference (3) and FIG. 4 shows this in detail. This construction allows the interventional cardiologist to make a telescopic adjustment of the device's total length and to adapt it to the anatomy of each patient, moving section (1b) which is inserted inside the lower end of the upper portion (2)

The other possible completion is the one in which the lower section (1) is unitary the upper section (2), forming only one piece.

From the material point of view, this device can be formed by the same mesh in both sections (1,2) or the lower portion (1) can be made of a more rigid mesh, while the upper portion (2) can be made of a more flexible and soft mesh. Thus it is important that the device of the invention can present a unique mesh of equal resistance along the device, or a mesh with different rigidity and elasticity.

Figure 3:
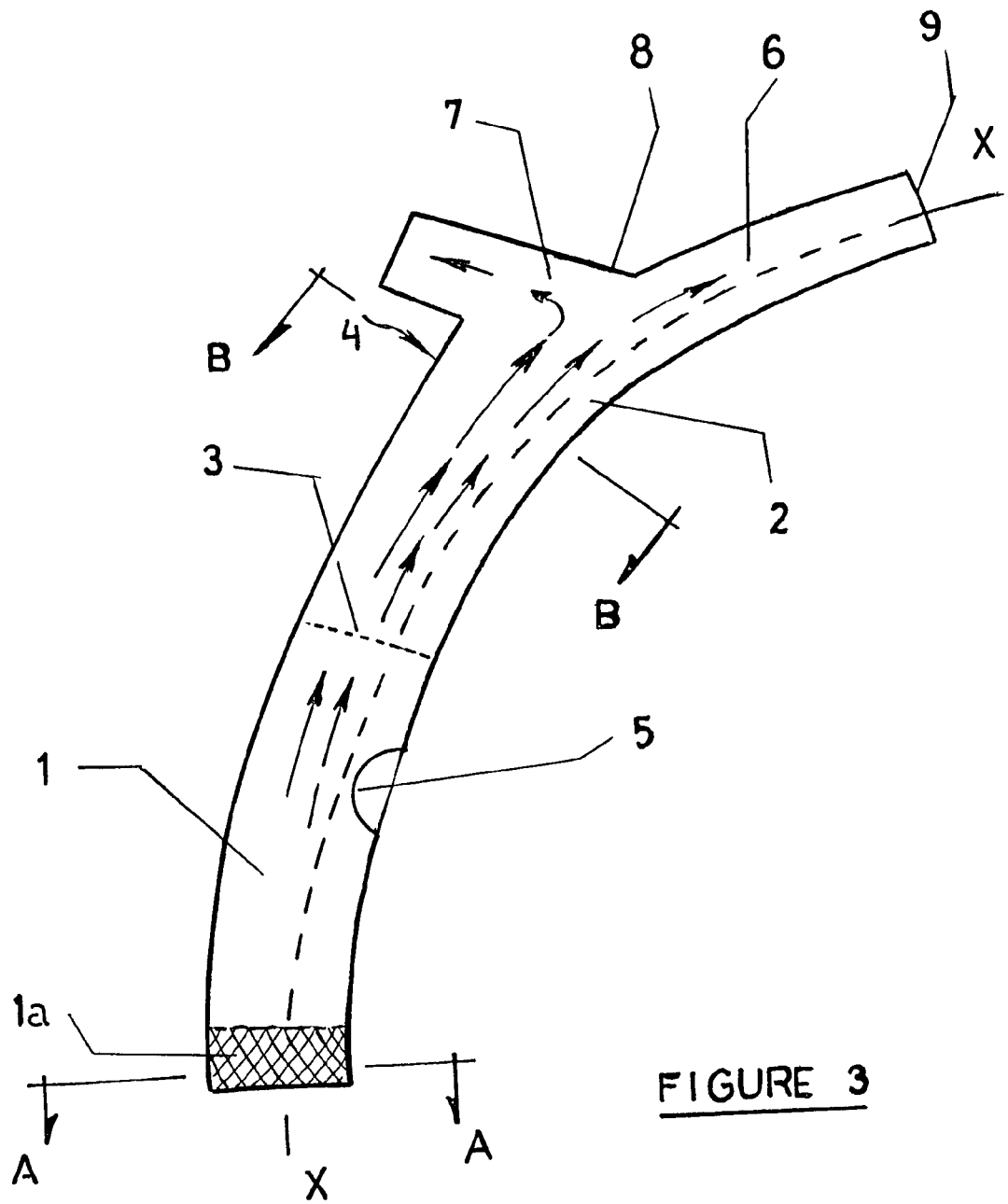
FIG. 3 shows a view in lateral elevation of one of the possible constructions of the invention.

The first portion (1) has a curvature between 35°-45°, the first section having in its lower end (1a) a transverse section that is substantially circular with a diameter between 16-20 mm, which is shown in FIG. 8, while in its upper end this first section presents a transverse section that is progressively flattened and that has a substantially oval shape, which is shown in FIG. 9 and in FIG. 3.

One of the important characteristics of this invention in one of its preferred constructions is that the transverse sections along the XX axis have substantially the same area from the lower end (1a) up to an area (4) below the bifurcation described in more detail below because in this zone the device has to fit with the pulmonary artery and with the RPA whose average diameter is 12 mm, so that it must have an oval or elliptic section whose smallest diameter according to the Y axis of FIG. 9 is equivalent to 12 mm, which allows it to fit the bigger dimensions of the RPA, and thereby maintain a transverse section with the same area.

The side wall of this first section (1) is formed at least one hole or fenestration (5) of 4 mm diameter, which can be closed and which allows the conduit interior to communicate with the exterior.

After reaching this second section (2) at the section (4) in FIG. 3, this second section (2) bifurcates in two branches. One of these branches is longer, has a transverse sectional size which is substantially circular with a diameter between 10-13 mm, and follows the warped axis XX as shown at (6), so that it can fit snugly inside the LPA, establishing a hermetic tight relation with its internal walls, and closing the pulmonary artery entrance.

The other branch (7) is projected in the shape of a short extension of substantially circular transverse section with a diameter of 10-13 mm and obliquely diverging toward the posterior, forming with respect to the branch (6) of major length a distorted Y. This short branch (7) fits into the beginning of the RPA.

In the device the first section (1) length is between 60-75 mm while the major length branch (6) of the second section is between 18-25 mm, and the length of the short bifurcated extension (7) is between 4-8 mm.

Another important aspect of this invention is that it provides a distribution of the RPA and LPA flows balanced according to the physiological model. To do this according to the invention the branch of major length (6) should be the followed by of the warped axis XX, but from this bifurcation the transverse section (6) is substantially circular with a diameter about 12 mm. Starting from an elliptic tubular conduit (4) with an area equivalent to a circle with an average diameter of 18 mm, the transverse area (6) is notably smaller than the transverse section (2) in zone (4), so the short extension (7) which starts in this area (4) with a cross-sectional size or transverse area equivalent to a circle of a diameter of about 18 mm. The transition between these two transverse areas is at the extension wall (8) that is substantially perpendicular to the blood flow which runs through (1,2), forcing part of the flow to divert through (7) when it collides with (8).

In another words, the short extension (7) in its bifurcation with respect to the branch of major length (6) defines a wall portion (8) which blocks between 50%-70% of the blood flow, which runs up in the tubular conduit (1,2) from the lower end, as indicated by the arrows in FIGS. 3 and 6. This short extension can be covered, or can be a mesh without a coating.

In another construction of the invention, the branch (6) of the bifurcation has a transverse section slightly decreasing to its free end, with the aim of being applied in cases in which it is necessary to limit in a small amount the blood volume towards LPA, and to increase the flow towards RPA, according to the Interventional Cardiologist's criterion.

FIG. 5 shows the device of FIG. 3, projected with a lateral elevation from its left side. It is emphasized that the XX axis is warped in space, and the end (9) of the branch (6) runs backwards like the branch (7). It can also be seen in this figure that the transverse sections of section (2) are flattened to gain a smaller diameter compatible with LPA diameter.

FIG. 6 is an idealization which shows the area relationships between the different device branches, showing the sections which form a slight lateral perspective, as if they had straight axes and constant and circular transverse section.

This situation shows the XX axis aligned with section (6) of the bifurcation, which is moved towards a lateral of the device, while the branch (7) of the same bifurcation is aligned with another axis. These two axes represent the blood flows that separate and move through (6) and (7). In the bifurcation quoted above, it is important to stress that the portion (2) has a transverse area (10) joining the transverse areas (11) and (12) of sections (6) and (7). It can be seen that areas (11, 12) are smaller in magnitude that area (10), in a proportion substantially coincident with the flow rate, which derives from branches (6) or (7).

Figure 7:
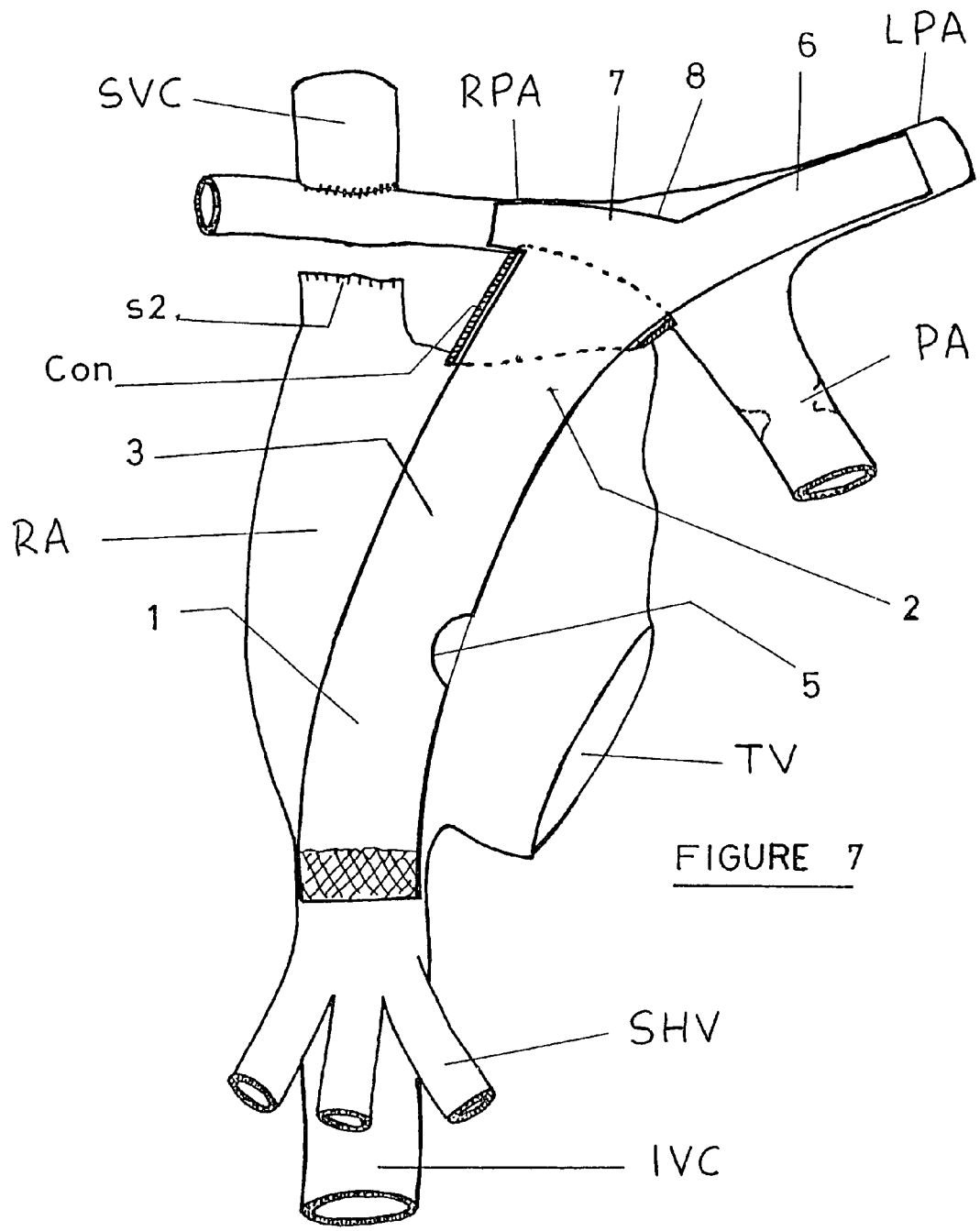
FIG. 7 shows the device lodged inside the FIG. 2 heart.

FIG. 7 shows the device of the invention placed inside RA, according to one of the several possible techniques, not being either unique nor exclusive. This technique attaches the appendage end (Ra) with the pulmonary trunk neck with the RPA oriented towards the LPA. This attachment can be made by suturing the appendage end and then making a puncture from inside the RA accommodate the device bifurcation (6,7) or suturing a short conduit (Con) connecting the Ra with the RPA, puncturing or cutting and passing the device through that conduit (See FIG. 7).

The connection site is the joint, established beforehand by surgery, between the right appendage (Ra) and the right pulmonary artery (RPA) close to the pulmonary trunk.

This connection avoids the sinus node and the complication caused by conduction disorders. The surgery technique, during the previous Glenn procedure, should contemplate a reinforcement with Gore-Tex™ through an anastomosis of both anatomical references and attaching the surface of the upper right appendage with the lower one of the proximal right branch. The "floor" of the right branch will open freely and the appendage "vault" will divide into cross sections with an elliptic area and then these incisions should be sutured.

In its unified version, the device is autoexpandable, it releases when an installation sheath is withdrawn, when the device is deployed from its distal end. It will be installed according to the anatomical features, up to the bifurcation site. The deployment device arm mechanism or the right branch of the bifurcation assumes the illustrated shape by elastic recovery of its shape and orientation. This happens because it is perpendicularly telescoped inside the device tubular body. The primary anchorage is caused when both branches are fitted in the installation sheath. The secondary anchorage is at IVC level.

When made of two parts (FIG. 4), the distal or upper portion (2) is autoexpandable and is inserted in the pulmonary branches, as depicted above. The lower or proximal section (1), the one that has the fenestration, can be made of a more rigid material, or with a less flexible material, and can be deployed with a balloon, by inserting it inside the upper portion (2).

The invention claimed is:

1. A fenestrated asymmetric intracardiac device for the completion of total cavopulmonary anastomosis through cardiac catheterization, the device comprising a bifurcated tubular conduit formed by a first lower section and a second upper section both centered on and extending alone a common warped axis having a radius of curvature between 35° and 45°, the first section being a tubular mesh covered at least in some parts by an impermeable polymer and having
  a lower end of substantially circular cross-sectional shape with a diameter between 16-20 mm,
  an upper end having a progressively flattened and a substantially oval cross-sectional shape, the upper end and lower end both being of substantially the same cross-sectional area along their full axial lengths, and
  a wall formed with at least one closable fenestration that connects an interior of the conduit with the exterior,
the second upper section being a tubular mesh covered at least partially by an impermeable polymeric material and having a cross-sectional shape that is oval and tapers upward to a diameter of between 10-13 mm, the second section bifurcating upward into two branches one of which is longer than the other, the longer branch extending along the warped axis, the other branch being formed with a short laterally projecting extension of circular cross-sectional shape forming with the first lower portion a distorted "Y", each branch having a mesh at least partially covered by an impermeable polymeric material and being formed unitarily with the second upper section, the conduit being between 60-75 mm long overall, the one branch being between 18-25 mm long, and the other branch being between 4-8 mm long, the short branch having a wall that intercepts between 50%-70% of blood flowing up through the tubular conduit from its lower end, the lower end being constructed for connection with a lower vena cava and a hepatic vena with the upper and lower sections of the tubular conduit configured to be lodged inside the right atrium, one branch being sized to be tightly lodged inside a left pulmonary artery and forming an obstruction with regard to a main pulmonary artery, the other branch being configured to be lodged at a base of a right pulmonary artery.

2. The fenestrated asymmetric intracardiac device according to claim 1 wherein the first lower section and the second upper section form a one-piece tubular body made at least partially of a series of threads forming a mesh.

3. The fenestrated asymmetric intracardiac device according to claim 1 wherein the first lower section has a mesh part that is independent of the second upper section, the first section being axially deployable within the second section, whereby the first section can be telescoped to variable length.

4. The fenestrated symmetric intracardiac device according to claim 1 wherein the first lower section has a mesh made of more resistant filaments than the second section so that first lower section is of less flexibility than the second upper section.

5. The fenestrated asymmetric intracardiac device according to claim 1 wherein the mesh of the lower end of the first section is free of the cover of impermeable polymeric material and is thereby rendered permeable to blood flow from a lower vena cava and hepatic vena.

6. The fenestrated asymmetric intracardiac device according to claim 1 wherein the one branch of the bifurcation is formed by a mesh made of threads covered by an impermeable polymeric material, the one branch forming with the second upper section a tubular wall impermeable to blood flow, the other branch not being covered by the impermeable material and being permeable.

7. The fenestrated asymmetric intracardiac device according to claim 1 wherein the mesh is made of linked metallic threads forming an elastically deformable conduit, the impermeable polymeric material being polytetrafluoroethylene.

* * * * *